(12) United States Patent
Obi et al.

(10) Patent No.: US 9,770,448 B1
(45) Date of Patent: Sep. 26, 2017

(54) COMPOSITIONS AND METHODS FOR TREATMENT OF BOWEN'S DISEASE AND RELATED DISEASES

(71) Applicants: Justice E. Obi, St. Albans, NY (US);
James K. Bashkin, St. Louis, MO (US)

(72) Inventors: Justice E. Obi, St. Albans, NY (US);
James K. Bashkin, St. Louis, MO (US)

( * ) Notice: Subject to any disclaimer, the term of this patent is extended or adjusted under 35 U.S.C. 154(b) by 0 days.

(21) Appl. No.: 15/199,240

(22) Filed: Jun. 30, 2016

(51) Int. Cl.
| | | |
|---|---|---|
| *A01N 43/42* | (2006.01) | |
| *A61K 31/47* | (2006.01) | |
| *A61K 31/4706* | (2006.01) | |
| *A61K 31/4164* | (2006.01) | |
| *A61K 9/02* | (2006.01) | |
| *A61K 9/06* | (2006.01) | |
| *A61K 9/00* | (2006.01) | |
| *A61K 31/167* | (2006.01) | |

(52) U.S. Cl.
CPC ........ *A61K 31/4706* (2013.01); *A61K 9/0014* (2013.01); *A61K 9/0034* (2013.01); *A61K 9/0053* (2013.01); *A61K 9/02* (2013.01); *A61K 9/06* (2013.01); *A61K 31/167* (2013.01); *A61K 31/4164* (2013.01)

(58) Field of Classification Search
None
See application file for complete search history.

(56) References Cited

U.S. PATENT DOCUMENTS

| | | | |
|---|---|---|---|
| 2014/0011838 A1* | 1/2014 | Obi | A61K 31/4706 514/313 |
| 2014/0011839 A1* | 1/2014 | Obi | A61K 31/47 514/313 |

* cited by examiner

*Primary Examiner* — Jeffrey H Murray
(74) *Attorney, Agent, or Firm* — Dale J. Ream

(57) ABSTRACT

Compositions and methods for the treatment of Bowen's disease, an orphan disease, are described. In addition, compositions and methods for the treatment of recurrent respiratory papillomatosis (RRP), an orphan disease, are described. Compositions and methods for the treatment of stage 1 melanoma are also described. The compositions comprise one or more active ingredients selected from the group consisting of: chloroquine, amodiaquine, and an antibiotic such as metronidazole. The methods comprise administering a therapeutically effective amount of such compositions to a subject in need thereof.

39 Claims, No Drawings

COMPOSITIONS AND METHODS FOR TREATMENT OF BOWEN'S DISEASE AND RELATED DISEASES

TECHNICAL FIELD

The present invention relates generally to the field of skin diseases and more specifically to compositions and methods for the treatment of Bowen's disease and related diseases.

BACKGROUND

Bowen's disease and related diseases such as recurrent respiratory papillomatosis (RRP) are rare diseases, for which the medical need has not yet been met, and require drugs to cure or treat them. Stage 1 melanoma is a disease which is often initially treated by surgery. Each of these diseases would benefit from new treatments. Bowen's disease may also be identified as an orphan disease, referring to a disease or condition that affects fewer than 200,000 people and, as a result, is often overlooked as providing sufficient incentive to researchers and enterprises to develop pharmaceuticals for treatment.

Bowen's disease (also known as "squamous cell carcinoma in situ") is a very early form of skin cancer. The main visible symptom is a red, scaly patch on the skin. Bowen's disease involved abnormal growth of the squamous cells, in the outermost layer of skin. Sometimes, the cancerous cells spread along the skin's surface, but it is usually very slow-growing and may not change for years. Occasionally (in 3-5% of patients), Bowen's disease infiltrates the deeper layers of skin and turns into a more serious type of skin cancer. However, the disease is manageable and there is only a risk if it is left undiagnosed or untreated.

Recurrent respiratory papillomatosis (RRP) disease is also known as "laryngeal papillomatosis". It is caused by HPV, typically HPV6 and 11, and involves formation of generally nonmalignant tumors on the larynx or vocal chords, but can spread to the trachea, bronchi and even to the lungs. This rare disease is typically fatal and can require large numbers of surgeries per year to keep the airway open. Children can contract RRP in the birth canal from vaginal delivery when mothers have active cases of condyloma, and adults also contract the disease.

Stage I malignant melanoma (sometimes called a localized melanoma) is a cancer in epidermis (the outer layer of the skin) and/or the dermis (upper part of the inner layer of skin), but which has not spread to lymph nodes or anywhere else in the body. An important feature of melanoma is the thickness of the melanoma ("Breslow thickness," which is measured in millimeters). Based on the thickness of the tumor, a melanoma is categorized into 3 main groups: (1) thin melanomas, where the thickness is less than or equal to 1 mm; (2) intermediate thickness melanomas, where the thickness is between 1 mm to 4 mm; and (3) thick melanomas, where the thickness is greater than 4 mm. Thicker melanomas have a greater chance of spread to sites beyond the initial tumor and a greater chance of recurrence. Generally, when a melanoma spreads, it spreads to lymph nodes in the region of the primary tumor first. Stage 1 melanoma is often treated with surgery. The patient would undergo an operation to remove a larger area of healthy tissue around the melanoma. This removal of surrounding tissue is called a wide local excision. The amount of tissue removed in a wide local excision depends on the thickness of the melanoma. While this is a small operation, alternative non-surgical remedies would be desirable in treating melanomas detected at such an early stage.

SUMMARY OF THE INVENTION

The current disclosure provides compositions and methods for the treatment of Bowen's disease, recurrent respiratory papillomatosis (RRP) and melanoma (at stage 1). The present disclosure resides in the discovery that one or a combination of the known compounds chloroquine and amodiaquine, or pharmaceutically acceptable salts thereof, all of which have been used previously as antimalarial agents and/or to treat disorders of the immune system, also have utility in treating Bowen's disease, recurrent respiratory papillomatosis (RRP) and melanoma (at stage 1). In some cases, one or a combination of these compounds can be effectively used in further combination with an antibiotic such as metronidazole.

In another aspect, the current disclosure provides compositions that comprise one or more of chloroquine, amodiaquine, and metronidazole; and methods of using these compositions for the treatment of Bowen's disease. In a further aspect, the current disclosure provides methods of using compositions comprising metronidazole for the treatment of Bowen's disease.

In yet another aspect, the current disclosure provides compositions that comprise one or more of chloroquine, amodiaquine, and metronidazole, and methods of using these compositions for the treatment of recurrent respiratory papillomatosis (RRP).

In a further aspect, the current disclosure provides compositions that comprise one or more of chloroquine, amodiaquine, and metronidazole; and methods of using these compositions for the treatment of stage 1 melanoma.

DETAILED DESCRIPTION OF THE PREFERRED EMBODIMENT

The disclosure provides compositions that comprise one or more active ingredients from the group consisting of chloroquine, amodiaquine, and an antibiotic. According to some embodiments, the antibiotic is metronidazole.

The disclosure provides methods of using these compositions for the treatment of Bowen's disease. The disclosure also provides methods of using these compositions for the treatment of RRP. The disclosure further provides methods of using these compositions for the treatment of stage 1 melanoma.

The molecular structures of chloroquine (IUPAC name: (RS)—N'-(7-chloroquinolin-4-yl)-N,N-diethyl-pentane-1,4-diamine), hydroxychloroquine (IUPAC name: (RS)-2-[{4-[(7-chloroquinolin-4-yl)amino]pentyl}(ethyl)amino]ethanol) and amodiaquine (IUPAC name: 4-[(7-chloroquinolin-4-yl)amino]-2-[(diethylamino)methyl]phenol) are provided below, as Formula I, Formula II, and Formula III, respectively.

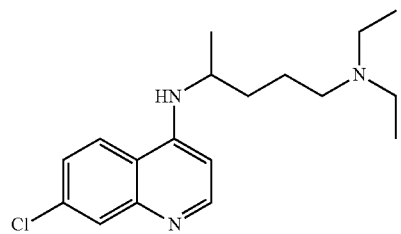

Formula I

-continued

Formula II

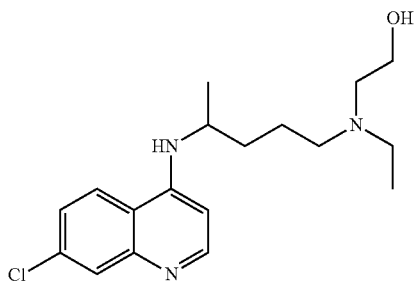

Formula III

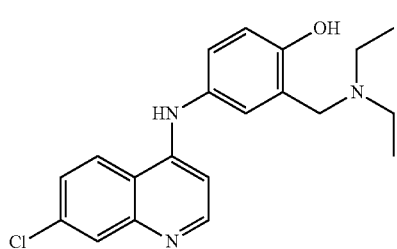

Formula IV

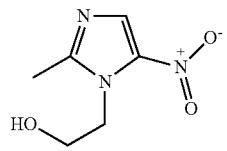

As is known, and as can be seen in the structural formulas set out above, these three compounds are related to one another in that their structures have a heterodicyclic portion in common, namely, the 7-chloro derivative of the 4-aminoquinoline moiety. Chloroquine (Formula I) has been marketed under the brand name RESOCHIN, while hydroxychloroquine (Formula II) has been marketed under the brand name PLAQUENIL, and amodiaquine (Formula III) has been marketed under the brand name CAMOQUIN. Chloroquine is commercially available as the pharmaceutically acceptable salt chloroquine phosphate, and may be purchased in solid (tablet) form from a wide variety of sources such as Ohm Laboratories, Inc of North Brunswick, N.J., U.S.A., while a ready-made aqueous solution may be purchased from a wide variety of sources, including Sal Parenterals (P) Ltd., of Hyderabad, India, or Scott Edil Pharmacia Ltd., of Jhannajri, India. Hydroxychloroquine, in solid (tablet) form, is commercially available as the pharmaceutically acceptable salt hydroxychloroquine sulfate, and may be purchased from a wide variety of sources such as West-Ward Pharmaceutical Corporation of Eatontown, N.J., U.S.A. Amodiaquine, in solid (tablet) form, is commercially available as the pharmaceutically acceptable salt amodiaquine hydrochloride, and may be purchased from a wide variety of sources, including Parke, Davis & Company, a division of Pfizer Inc., headquartered in New York, N.Y., U.S.A.

In certain embodiments, the compositions of the disclosure comprise an antibiotic. In some embodiments, the antibiotic is metronidazole. Metronidazole is a nitroimidazole antibiotic and antiprotozoal medication. It can be given via oral or parenteral (including topical, intravenous, and intravaginal) administration. Metronidazole has been marketed under the names METROGEL, FLAGYL, NORITATE, METROCREAM, ROSADAN, and METROLOTION, among others. The molecular structure of metronidazole (IUPAC name: 2-(2-methyl-5-nitro-1H-imidazol-1-yl)ethanol) is provided below, as Formula IV.

In certain embodiments, the compositions of the disclosure comprise either chloroquine (Formula I) alone or amodiaquine (Formula III) alone as the active ingredient, or chloroquine combined with amodiaquine, or chloroquine combined with metronidazole (Formula IV), or amodiaquine combined with metronidazole, or chloroquine combined with both amodiaquine and metronidazole, as the active ingredients.

In general, as mentioned above and as set forth in further detail below, the methods of the disclosure comprise, in certain embodiments, administering the pharmaceutical compositions of the disclosure comprising the active ingredient or ingredients to a subject such as a human being using one or more of the specific routes of administration, which include direct topical (epicutaneous) administration, in forms such as gel, douche, cream, lotion, solution, spray, soap or other bathing apparatus; transdermal administration, in the form of a patch; transmucosal administration (also known as pharmaceutical pessary delivery) through the vagina or rectum, in the form, for example, of an ovule or a suppository, including a vaginal suppository; respiratory administration, such as delivery via inhalation through the nostrils and nasal passages of aerosol droplets produced, for example, with the aid of a nebulizer; and infusion under the skin in the form of an intra-epidermal injection.

Although the compositions and methods of the disclosure will be illustratively described hereinafter with reference to topical, transmucosal, oral and other routes of administration, it should be understood that the disclosure is not limited to the specific cases described, but extends also to the use of other compatible routes for administering pharmaceutical compositions according to the disclosure, as will be evident to those skilled in the art, including but not limited to other topical and/or parenteral routes, such as buccal, conjunctival, endotracheal, intramuscular, intravascular, laryngeal, or ophthalmic, or even enteral (oral) routes, any one or more of which may be used. Suitable formulations for any route of administration that is ultimately selected are known and are described in well-known texts, including for example Remington, The Science and Practice of Pharmacy, 21st edition, 2005, Mack Publishing Company, Easton, Pa., and therefore such formulations may easily be prepared by those of ordinary skill in the art.

It is well understood, however, that proper dosages of any medication may vary from one individual to another, depending on many factors such as the intensity of the affliction and the selected route of administration, as well as the weight, age and gender of the subject or patient. Therefore, the effective dosages of the pharmaceutical compositions of the present disclosure should be determined by a specialist in this matter, such as a medical doctor or other health care provider, depending on these and other parameters. Nevertheless, for the sake of illustration only, exemplary formulations, preparation procedures and dosages, for topical, transmucosal, and other routes of administration, are provided herein for the sake of guidance.

When the compositions of the disclosure comprising one or more of chloroquine, amodiaquine and metronidazole as the only active ingredient(s) are to be administered topically (epicutaneously), in the form of a gel or a spray, the compositions may comprise chloroquine and/or amodiaquine and/or metronidazole plus optional non-active ingredients. The non-active ingredients may comprise sodium carboxymethylcellulose, a preservative (for example, methylparaben, for example at 0.5%), purified water, Versatile gel base, as well as ethyl alcohol and peppermint spirit oil, and the gel form may additionally comprise lidocaine jelly or ointment, while the spray form may additionally comprise lidocaine as a 2% solution. All of the non-active ingredients are conventional and are available commercially from a wide variety of sources. The non-active ingredients are exemplary only, but are included for the following purposes: the lidocaine functions as an analgesic, the ethyl alcohol functions as an antiseptic, while the peppermint spirit oil functions to provide a pleasing odor. The compositions of the disclosure comprising one or more of chloroquine, amodiaquine and metronidazole are also provided in suppository and douche forms. The suppository forms may comprise chloroquine and/or amodiaquine and/or metronidazole plus optional non-active ingredients. The douche forms may comprise chloroquine and/or amodiaquine and/or metronidazole plus optional non-active ingredients. The non-active ingredients in the suppository form may comprise Polybase (for example, containing PEG 400, PEG 8000 and Polysorbate 80), and citric acid, while the non-active ingredients in the douche form may comprise purified water for irrigation, sodium chloride (for example 0.9%, or normal saline), citric acid, a preservative (for example, sodium benzoate).

Particular embodiments of compositions for the gel, suppository and douche forms may be prepared as set forth in the Formulation Examples below.

The gel forms of these medications may be administered to a subject as follows: The affected areas are first cleaned with one or more alcohol swabs. Thereafter, an amount of the gel approximately equal to the surface area of each affected area (or an amount equal to the surface area of the tip of a finger) is applied to the affected area, after which that area may optionally be covered with a sterile bandage. The gel form may be administered to the subject in the foregoing manner once or twice a day, for approximately one to four weeks, until return of the affected area(s) to a normal skin appearance.

The spray forms of these medications may be administered to a subject in the same manner, although the dosage may be two puffs applied to the affected areas once or twice daily.

The suppository forms for vaginal administration of these compositions may be administered to a subject by placing the "bullet", or suppository, into the vagina. The suppository form for vaginal administration may be administered to the subject once or twice a day, for approximately one to four weeks, until return of the affected area(s) to a normal skin appearance. The suppository form for vaginal administration may be administered before or at bedtime.

The douche forms for vaginal or oral administration of these compositions may be administered vaginally using a bottle or other suitable apparatus. It may also be administered orally, where needed, by gargling of the douche solution. Either form (as appropriate) may be administered to the subject once or twice a day, for approximately one to four weeks.

A. Terms, Definitions and Abbreviations

As used herein and unless otherwise expressly noted or required by the context, all percentages refer to percentages by weight (wt-%) of the total composition (w/w).

As used herein in connection with a measured quantity, for example weight, "about" refers to that variation in the measured quantity as would be expected by one skilled in the art exercising a level of care commensurate with the objective of the measurement and the equipment used, and includes uncertainties that may be introduced by mathematical rounding errors.

As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile may be used. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

B. Embodiments

The following examples are provided to further elucidate the advantages and features of the present application, but are not intended to limit the scope of the application. The examples are for the illustrative purposes only. USP pharmaceutical grade products were used in preparing the formulations described below.

FORMULATION EXAMPLES

The formulation percentage range covers from 2.5% to 25% of the active ingredient, whether it is one active ingredient or two active ingredients, or a mixture of three active ingredients.

For topical treatment of Bowen's disease (squamous cell carcinoma in situ) and other related diseases like RRP and melanoma (at stage one).

Gel Formula 1

For Chloroquine compounding, to make 10% gel tube of 60 grams:

| | |
|---|---|
| 1) Chloroquine phosphate pure powder 10% equals to | 7 grams |
| 2) Sodium Carboxymethyl-cellulose is | 1.2 grams |
| 3) Methylparaben (0.5%) (as preservative) is | 1.2 grams |
| 4) Purified water is | 10 ml |
| 5) Versatile gel base is | 41 grams (ml) |

Sufficient to make 60 gram tube gel of Chloroquine 10%. To be applied about 2 times a day for about 14 days to cover the affected area topically. The composition may be prepared by crushing the chloroquine phosphate tablets in a mortar or using chloroquine phosphate powder, and then adding each of the non-active ingredients, in the sequence listed above, sufficient to make a total of approximately 60 gm of the gel. The gel form may then be transferred to a tube or other appropriate container.

Gel Formula 2

For Chloroquine compounding, to make 10% gel of three compounds of 60 grams:

| | |
|---|---|
| 1) Chloroquine | 2.2 grams |
| 2) Amodiaquine | 2.2 grams |
| 3) Metronidazole | 2.2 grams |
| 2) Sodium Carboxymethyl-cellulose is | 1.2 grams |
| 3) Methylparaben (0.5%) (as preservative) is | 1.2 grams |
| 4) Purified water is | 10 ml |
| 5) Versatile gel base is | 41 grams (ml) |

Sufficient to make 60 gram tube gel. To be applied about 2 times a day for about 14 days to cover the affected area topically. The composition may be prepared by adding the chloroquine, amodiaquine and metronidazole, and then adding each of the non-active ingredients, in the sequence listed above, sufficient to make a total of approximately 60 gm of the gel. The gel form may then be transferred to a tube or other appropriate container.

Vaginal Suppository Formula 1

To formulate 24 bullet-shaped suppositories to treat Bowen's disease (squamous cell carcinoma in situ) and other related diseases like RRP and melanoma (at stage one).

| | |
|---|---|
| 1) Chloroquine | 6 grams of pure powder |
| 2) Polybase containing | PEG 400, PEG 8000 and Polysorbate 80 |
| 3) Citric acid powder | 1.5 grams |

Sufficient to make 24 bullet shaped vaginal suppositories. To be applied vaginally at bedtime for about 14 days. Optional active ingredient: Metronidazole—6 gram/60 ml in which each ml contains 100 mg of Metronidazole. The vaginal suppository composition may be prepared by adding the chloroquine (and metronidazole if included), and then adding each of the non-active ingredients, in the sequence listed above, sufficient to make the suppository.

Vaginal Suppository Formula 2

To formulate 24 bullet-shaped suppositories to treat Bowen's disease (squamous cell carcinoma in situ) and other related diseases like RRP and melanoma (at stage one).

| | |
|---|---|
| 1) Amodiaquine | 7 grams of pure powder |
| 2) Metronidazole | 6 grams |
| 2) Polybase containing | PEG 400, PEG 8000 and Polysorbate 80 |
| 3) Citric acid powder | 1.5 grams |

Sufficient to make 24 bullet shaped vaginal suppositories. To be applied vaginally at bedtime for about 14 days. The vaginal suppository composition may be prepared by adding the amodiaquine and metronidazole, and then adding each of the non-active ingredients, in the sequence listed above, sufficient to make the suppository.

Douche Solution

To make 10% Chloroquine douche in 4.5 oz (133 ml). To be applied vaginally or orally (for gargling) at bedtime for about 14 days.

| | |
|---|---|
| 1) Chloroquine | 15 gm pure powder |
| 2) Purified water for irrigation | 100 ml |
| 3) Purified Sodium Chloride 0.9% (normal saline) | 15 ml |
| 4) Citric acid | 2 ml |
| 5) Sodium benzoate (as preservative) | 1 ml |

Optional active ingredient: Metronidazole—6 gram/60 ml in which each ml contains 100 mg of Metronidazole. The douche composition may be prepared by adding the chloroquine (and metronidazole if included), and then adding each of the non-active ingredients, in the sequence listed above, sufficient to make the suppository.

TREATMENT EXAMPLES

In vivo experimental results which demonstrate the efficacy of the foregoing compositions are set forth below. Specifically, the following working examples illustrate both the manner in which a representative sample of the compositions of the present disclosure have been used in human subjects suffering from at least symptom associated with Bowen's disease, and the experimental results obtained, which demonstrate the efficacy of the disclosed compositions and methods.

Example 1

A 61 year old white Caucasian male who had been suffering from Bowen's disease for almost ten years presented with pink/red bumps on his arms and fingers with plaque and irregular thick borders and surface crusting and scaling with itching sensation at times. He was treated with a composition in gel form comprising chloroquine as the active ingredient (prepared in the manner set forth above for such compositions). This gel composition was applied to the affected area twice a day. After two weeks of treatment, the entire affected skin area returned to normal skin.

Example 2

An adult female of European descent with Bowen's disease presented with a localized, 7 centimeter plaque under the umbilical area with reddish color and thick borders. She was treated with a composition in gel form comprising chloroquine as the active ingredient (prepared in the manner set forth above for such compositions). The gel composition was applied to the affected area twice a day for two weeks. After treatment for two weeks, the reddish color disappeared and the plaque fell off from the affected area.

Example 3

A 26 year old Caucasian female with Bowen's disease for more than 5 years presented with lesions near her labia major and labia minor. She was treated with a composition in gel form comprising chloroquine as the active ingredient (prepared in the manner set forth above for such compositions). This gel composition was applied to the affected area twice a day. After two weeks of treatment, the affected skin area returned to normal skin. The woman's boyfriend also presented with Bowen's disease in his pubic area as a thick scar tissue with pinkish color. He was also treated with the composition in gel form comprising chloroquine as the active ingredient. After two weeks of twice daily treatment, his affected skin area also returned to normal skin.

Example 4

An adult female of Indian descent with Bowen's disease located in her genital area was treated with a composition in gel form comprising chloroquine as the active ingredient (prepared in the manner set forth above for such compositions). This gel composition was applied to the affected area twice a day. After less than 12 days of treatment, the affected skin area returned to normal skin.

Example 5

An adult female with Bowen's disease presented with warts. She was first ineffectively treated with a composition in gel form comprising chloroquine as the active ingredient, and further ineffectively treated with a composition in gel form comprising chloroquine and hydroxychloroquine as the active ingredients. However, after two weeks of twice daily treatment with a composition in gel form comprising chloroquine and metronidazole as the active ingredients, the affected skin area returned to normal skin.

Example 6

A 36 year old African female with Bowen's disease was treated using compositions in gel and douche forms comprising chloroquine and metronidazole as the active ingredient each twice a day for 21 days. After 21 days of treatment, the affected skin area returned to normal skin.

Example 7

Clinical trials of a gel composition comprising chloroquine prepared as described above, with an additional inactive ingredient lidocaine, were carried out for nine (9) patients with Bowen's disease. Treatment length ranged from 1 week to 6 weeks, with 8/9 patients achieving clearance of the disease. Results of these studies are shown in the table below.

| ID | Sex | Age | Diagnosis | Position | HPV type | Treatment length | Side effect | Results |
|---|---|---|---|---|---|---|---|---|
| 1 | F | 34 | Vulva condyloma accuminata | Vulva | 6 | 4 weeks | None | Disease cleared |
| 2 | M | 22 | Genital warts | Penis, feet | 6/11/44 | 5 weeks | None | Disease cleared |
| 3 | F | 23 | Vulva condyloma accuminata | Vulva | 6/58 | 2 weeks | None | Disease cleared |
| 4 | M | 36 | Flat wart | Face | 6 | 2 weeks | None | Disease cleared |
| 5 | M | 24 | condyloma accuminata | Feet | 44 | 4 weeks | None | No change |
| 6 | F | 19 | Vulva condyloma accuminata | Vulva | 11 | 4 weeks | None | Disease cleared |
| 7 | F | 24 | Vulva condyloma accuminata | Vulva | 11 | 1 week | None | Disease cleared |
| 8 | F | 28 | Vulva condyloma accuminata | Vulva | 11 | 1 week | None | Disease cleared |
| 9 | F | 40 | Vulva condyloma accuminata | Vulva | 6/11/52 | 6 weeks | Pain in first 2 days | Disease cleared |

Example 8

Application to Recurrent Respiratory Papillomatosis: In Vitro Chloroquine-Induced Killing of Laryngeal Keratinocytes In addition to the foregoing examples, in vitro experimental data have been obtained which indicate that the compositions and methods of the present disclosure can be used in the treatment of recurrent respiratory papillomatosis (RRPRRP) disease, which is also known as laryngeal papillomatosis. RRP is caused by human papillomavirus (HPV), typically HPV6 and HPV11, and involves formation of generally nonmalignant tumors on the larynx or vocal chords, and can spread to the trachea, bronchi and lungs. $HPV^+$ and $HPV^-$ laryngeal keratinocytes obtained from a recurrent respiratory papillomatosis patient were expanded on Mitomycin C-treated J2 3T3 feeder cell layers in E media with 10 uM Y27632 (ROCK inhibitor). These cells were then plated without feeder layers in 2.5 uM Y27632 and grown until they reached 90% confluency. At this point, fresh E media without Y27632 was added to the cells with increasing concentrations of chloroquine. Chloroquine concentrations used were 0 ug/ml, 2.5 ug/ml, 25 ug/ml, 250 ug/ml, 2.5 mg/ml and 25 mg/ml. Chloroquine powder (Sigma) was resuspended at 25 mg/ml in E media and was brought to pH 7 with 1N NaOH. Working dilutions were made with full E media. Cells were incubated for two days in chloroquine and then visually inspected for survival, as noted by (a) the presence of cells in the wells and (b) morphology of the cells.

$HPV^+$ and $HPV^-$ cells were killed at chloroquine concentrations of 250 ug/ml and higher. Both sets of cell survived 25 ug/ml concentrations of chloroquine. Thus, treatment of respiratory HPV infections with chloroquine may be useful.

Example 9

A 48 year old woman living in Wisconsin as a caregiver of European descent was referred by her doctor who could not help cure her Bowen's disease. According to her statement, she said that she was recently diagnosed with Bowen's disease inside her vagina and perianal which can lead to cervical cancer or vaginal cancer and also skin cancer of the genital area caused by type 16 of HPV. She had, in the past, tried a herbal remedy called shiitake mushrooms and also oregano oil, but no improvement was noticed. She claimed that she has been juicing, taking vitamins, and overall trying to eat better in order to stay healthy. She even quit smoking, but no help was coming from heaven or her doctor to cure her Bowen's disease. She is not quite sure what to believe and she made an important comment saying" "How come the U.S. government hasn't given me (Dr. Obi) a grant to develop the novel formulation if the drug works perfectly." She even said that I (Dr. Obi) will be a trillionaire if I were to find an honest investor.

Not withstanding, after 12 days of application of the gel by douching and applying on the skin she was declared cured and clean after she was re-tested and the results showed that she is HPV negative on both the external perianal and intravaginal lesion. Moreover she claimed to have a sore throat which is normally called orolaryngitis caused by Bowen's disease. The patient was treated with the honey sweet syrup formulation of the novel discovery, which she took orally, twice a day for five days, and the sore throat irritation was gone. If not treated with the present formulation the Bowen's disease would lead to cervical, vaginal, vulva, anal, and throat cancer.

Example 10

A 33 year old female from Skokie Ill. went to her Doctor to be tested in December 2015 due to she finding some perianal Bowen's disease lesions on her skin. According to her the result came back positive for perianal Bowen's disease for high risk HPV which lead her to believe that she might have more than one strain of the high risk type virus meaning that apart from the skin lesions she may also have intra-vaginal legions of the Bowen's disease. Her doctor said to her "I am sorry to hear of your diagnosis of perianal Bowen's disease; however, I am not able to help you because of some funding trouble, I have been a bit stuck in moving forward with my compound, which anyway is probably not effective against Bowen's disease. However, in the meantime I met Dr. Justice Obi, a medical doctor licensed in his native country Nigeria who discovered an already-approved drug that has a very high activity against Bowen's disease. Please contact him as soon as possible, his discovery is available free of charge but in return for a testimonial written about how it does or does not work. He has been so successful in treating many people and Dr. Obi's (the applicant) invention has already been in a clinical trial in China." This patient was a non smoker who tried over the counter drug called TCA (trichloroacetic acid) which made the Bowen's disease Lesion worse she said, but I told her that some drugs are worse than the disease; she laughed and she said agreed with me, without a doubt.

According to her statement, she said that she has been trying to eat healthier, take vitamins and sometimes exercise to try and boost her immune system. She has never smoked and she rarely drinks and she is very healthy otherwise, so with all these things happening with her she felt that she has a good chance of fighting the Bowen's disease naturally but that didn't work. She has two small children and she is constantly worried that she might not be there for them because of the possibility of developing cervical, or any kind of, cancer from the Bowen's disease. Notwithstanding, after a week and a half of application of the formulation at bedtime, her external skin lesions of Bowen's disease disappeared without a trace, including the intravaginal ones, as she wrote to me, "I am SOOOO happy and SOOOO grateful, for what you have done to me by giving me my life back again to live for my two children." She also took the honey sweet syrup of the gel orally and within 5 days the sore throat irritation was gone. If not treated with my novel discovery the Bowen's disease would have led to cervical, vaginal, vulvar, anal, and throat cancer.

Example 11

A Caucasian woman of 49 years old from Browns Summit North Carolina who works as a PT assistant (licensed PTA) in North Carolina with no allergies to any medication. She was diagnosed in 2013 with ASCUS and positive for HPV 31.

ASCUS is defined as an atypical squamous cells of undetermined significance ("ASCUS")—squamous cells are thin and flat and grow on the surface of a healthy cervix. In the case of ASCUS the Pap smear reveals slightly abnormal squamous cells of Bowen's disease origin, but the changes clearly suggest that precancerous cells are present or may not be present.

She assumed that she is at a greater risk of developing Bowen's disease, according to her statement, in that she began a relationship with a new person of UFO and after 2 months in the relationship she was diagnosed with HPV type 16 of Bowen's Disease. Of course she became distraught and confused she may develop cancer in the future. According to her statement she claimed not to have any immunodeficiency disorder but only a sore throat at times but after using my drug orally twice a day for 5 days the throat irritation was gone and she feels normal again and the Bowen's disease in the genital area also disappeared. If not treated with my novel formulation, the Bowen's disease would lead to cervical, vaginal, vulva, anal, and throat cancer. This could cost the US government billions of dollars for treatment for patients who develop stage 4 cancer.

Benefits of Use of the Present Invention

There are various types of treatment for Bowen's disease that have advantages and disadvantages. Choosing the best therapy option is critical and cost effective, which involves analysis of various factors such as lesion size, number, site, degree of functional impairment, modality availability, and cost effective because most treatment have a recurrence risk, follow up 6-12 months is also recommended to evaluate for recurrence. The following drugs are used for Bowen's disease but are not effective;

1) 5-Fluorouracil tablet and injection (also known as Hawaii 5-0)
2) Imiquimod cream
3) Photo dynamic therapy
4) Surgical removal by cauterization or Cryotherapy.

All have been used for the treatment of Bowen's disease with little or no success. However, the use of my novel formulation is an effective treatment which the Bowen's Disease cannot overcome. It will cost less money to treat someone topically with a gel of my novel formulation and within 6-12 days the Bowen's Disease is gone. It is much more cost effective formulation than other methods of treatment which in turn will save billions of dollars in healthcare for the US government, insurance companies, and consumers.

Although the disclosed compositions and methods have been described with reference to the above examples, it will be understood that modifications and variations are encompassed within the spirit and scope of the present disclosure.

What is claimed is:

1. A method for the treatment of Bowen's disease in a subject in need thereof, comprising administering to the subject a pharmaceutical composition comprising one or more compounds from the group consisting of: chloroquine, amodiaquine, and pharmaceutically acceptable salts thereof.

2. The method of claim 1, wherein the pharmaceutical composition further comprises an antibiotic.

3. The method of claim 2, wherein the antibiotic is metronidazole.

4. The method of claim 1, wherein the pharmaceutical composition comprises chloroquine or a pharmaceutically acceptable salt thereof.

5. The method of claim 1, wherein the pharmaceutical composition comprises chloroquine or a pharmaceutically acceptable salt thereof, and metronidazole.

6. The method of claim 1, wherein the pharmaceutical composition comprises amodiaquine or a pharmaceutically acceptable salt thereof, and metronidazole.

7. The method of claim 1, wherein the pharmaceutical composition comprises chloroquine or a pharmaceutically acceptable salt thereof, amodiaquine or a pharmaceutically acceptable salt thereof, and metronidazole.

8. The method of claim 1, wherein the pharmaceutical composition is in a gel, suppository, or douche formulation.

9. The method of claim 1, wherein the pharmaceutical composition is administered to the subject topically, vaginally, or orally.

10. The method of claim 1, wherein the pharmaceutical composition is administered to the subject once per day.

11. The method of claim 1, wherein the pharmaceutical composition is administered to the subject twice per day.

12. The method of claim 1, wherein the pharmaceutical composition is administered to the subject for at least 1 week.

13. The method of claim 1, wherein the pharmaceutical composition is administered to the subject for at least 2 weeks.

14. A method for the treatment of recurrent respiratory papillomatosis (RRP) in a subject in need thereof, comprising administering to the subject a pharmaceutical composition comprising one or more compounds from the group consisting of: chloroquine, amodiaquine, and pharmaceutically acceptable salts thereof.

15. The method of claim 14, wherein the pharmaceutical composition further comprises an antibiotic.

16. The method of claim 15, wherein the antibiotic is metronidazole.

17. The method of claim 14, wherein the pharmaceutical composition comprises chloroquine or a pharmaceutically acceptable salt thereof.

18. The method of claim 14, wherein the pharmaceutical composition comprises chloroquine or a pharmaceutically acceptable salt thereof, and metronidazole.

19. The method of claim 14, wherein the pharmaceutical composition comprises amodiaquine or a pharmaceutically acceptable salt thereof, and metronidazole.

20. The method of claim 14, wherein the pharmaceutical composition comprises chloroquine or a pharmaceutically acceptable salt thereof, amodiaquine or a pharmaceutically acceptable salt thereof, and metronidazole.

21. The method of claim 14, wherein the pharmaceutical composition is in a gel, suppository, or douche formulation.

22. The method of claim 14, wherein the pharmaceutical composition is administered to the subject topically, vaginally, or orally.

23. The method of claim 14, wherein the pharmaceutical composition is administered to the subject once per day.

24. The method of claim 14, wherein the pharmaceutical composition is administered to the subject twice per day.

25. The method of claim 14, wherein the pharmaceutical composition is administered to the subject for at least 1 week.

26. The method of claim 14, wherein the pharmaceutical composition is administered to the subject for at least 2 weeks.

27. A method for the treatment of stage 1 melanoma in a subject in need thereof, comprising administering to the subject a pharmaceutical composition comprising one or more compounds from the group consisting of: chloroquine, amodiaquine, and pharmaceutically acceptable salts thereof.

28. The method of claim 27, wherein the pharmaceutical composition further comprises an antibiotic.

29. The method of claim 28, wherein the antibiotic is metronidazole.

30. The method of claim 27, wherein the pharmaceutical composition comprises chloroquine or a pharmaceutically acceptable salt thereof.

31. The method of claim 27, wherein the pharmaceutical composition comprises chloroquine or a pharmaceutically acceptable salt thereof, and metronidazole.

32. The method of 27, wherein the pharmaceutical composition comprises amodiaquine or a pharmaceutically acceptable salt thereof, and metronidazole.

33. The method of claim 27, wherein the pharmaceutical composition comprises chloroquine or a pharmaceutically acceptable salt thereof, amodiaquine or a pharmaceutically acceptable salt thereof, and metronidazole.

34. The method of claim 27, wherein the pharmaceutical composition is in a gel, suppository, or douche formulation.

35. The method of claim 27, wherein the pharmaceutical composition is administered to the subject topically, vaginally, or orally.

36. The method of claim 27, wherein the pharmaceutical composition is administered to the subject once per day.

37. The method of claim 27, wherein the pharmaceutical composition is administered to the subject twice per day.

38. The method of claim 27, wherein the pharmaceutical composition is administered to the subject for at least 1 week.

39. The method of claim 27, wherein the pharmaceutical composition is administered to the subject for at least 2 weeks.

* * * * *